US011684704B2

United States Patent
Hettler

(10) Patent No.: US 11,684,704 B2
(45) Date of Patent: Jun. 27, 2023

(54) AUTOCLAVABLE MEDICAL DEVICE AND ACTUATION MEANS FOR AN AUTOCLAVABLE MEDICAL DEVICE

(71) Applicant: SCHOTT AG, Mainz (DE)

(72) Inventor: Robert Hettler, Kumhausen (DE)

(73) Assignee: SCHOTT AG, Mainz (DE)

( * ) Notice: Subject to any disclaimer, the term of this patent is extended or adjusted under 35 U.S.C. 154(b) by 359 days.

(21) Appl. No.: 16/882,830

(22) Filed: May 26, 2020

(65) Prior Publication Data

US 2020/0282112 A1    Sep. 10, 2020

Related U.S. Application Data

(63) Continuation of application No. PCT/EP2018/081439, filed on May 31, 2019.

(30) Foreign Application Priority Data

Nov. 23, 2017 (DE) ..................... 10 2017 127 723.4

(51) Int. Cl.
 *H01H 9/04* (2006.01)
 *A61L 31/14* (2006.01)
 (Continued)

(52) U.S. Cl.
 CPC ............ *A61L 31/14* (2013.01); *A61B 5/0071* (2013.01); *A61B 5/681* (2013.01); *A61B 18/14* (2013.01);
 (Continued)

(58) Field of Classification Search
 CPC ...... A61L 31/14; A61L 31/022; A61L 31/026; A61L 2202/24; A61L 2/07; A61L 2/26;
 (Continued)

(56) References Cited

U.S. PATENT DOCUMENTS 5,609,561 A    3/1997  Uehara
6,076,197 A *  6/2000  Yeung ................. A47K 13/302
                                                    4/233
(Continued)

FOREIGN PATENT DOCUMENTS

CN    102671299    9/2012
CN    107001117    8/2017
(Continued)

OTHER PUBLICATIONS

English translation of Written Opinion from corresponding International Application PCT/EP2018/081439 dated Feb. 21, 2019, 8 pages.
(Continued)

*Primary Examiner* — Thuy N Pardo
(74) *Attorney, Agent, or Firm* — Ruggiero McAllister & McMahon LLC

(57) ABSTRACT

An autoclavable medical device is provided that includes a metal housing having an electrical conductor embedded in an inorganic fixing material. The conductor and fixing material define an electrical feedthrough that extends from an interior of the housing through at least a portion of the fixing material. The electrical feedthrough forms part of a sensor of an actuation means for the autoclavable medical device.

18 Claims, 6 Drawing Sheets

(51) Int. Cl.
    *A61B 90/30*    (2016.01)
    *A61B 5/00*    (2006.01)
    *A61B 18/14*    (2006.01)
    *A61B 18/20*    (2006.01)
    *A61C 3/02*    (2006.01)
    *A61L 31/02*    (2006.01)
    *H02G 3/22*    (2006.01)
    *G04C 3/00*    (2006.01)
    *A61B 17/14*    (2006.01)
    *A61B 17/16*    (2006.01)
    *A61B 18/00*    (2006.01)
    *A61C 13/15*    (2006.01)

(52) U.S. Cl.
    CPC .............. *A61B 18/20* (2013.01); *A61B 90/30* (2016.02); *A61C 3/02* (2013.01); *A61L 31/022* (2013.01); *A61L 31/026* (2013.01); *G04C 3/002* (2013.01); *H02G 3/22* (2013.01); *A61B 17/14* (2013.01); *A61B 17/1615* (2013.01); *A61B 17/1659* (2013.01); *A61B 2018/00589* (2013.01); *A61C 19/003* (2013.01)

(58) Field of Classification Search
    CPC ....... A61B 5/0071; A61B 5/681; A61B 18/14; A61B 18/20; A61B 90/30; A61B 17/14; A61B 17/1615; A61B 17/1659; A61B 2018/00589; A61B 5/0531; A61B 5/6887; A61B 90/08; A61B 2017/00017; A61B 2090/0813; A61C 19/003; A61C 3/02; G04C 3/002; H02G 3/22; H01H 13/86; H01H 2215/008
    USPC ..... 200/302, 302.1, 188, 237, 305; 600/424; 422/186.29
    See application file for complete search history.

(56) References Cited

U.S. PATENT DOCUMENTS

| | | | |
|---|---|---|---|
| 10,973,937 B1 * | 4/2021 | Ricciardi | A61L 2/16 |
| 2003/0152356 A1 | 8/2003 | Fritz | |
| 2007/0085496 A1 | 4/2007 | Philipp | |
| 2010/0247403 A1 * | 9/2010 | Hancock | A61L 2/14 |
| | | | 422/186.29 |
| 2012/0000756 A1 | 1/2012 | Schnitzler | |
| 2012/0193118 A1 | 8/2012 | Kempf | |
| 2015/0150646 A1 | 6/2015 | Pryor | |
| 2015/0238277 A1 * | 8/2015 | Ritchey | A61B 5/1127 |
| | | | 600/424 |
| 2016/0064167 A1 | 3/2016 | Lyszus | |
| 2016/0162256 A1 | 6/2016 | Komaromi | |
| 2016/0225363 A1 * | 8/2016 | Ishida | G03G 21/1619 |
| 2016/0324996 A1 * | 11/2016 | Bilenko | A61L 2/24 |
| 2017/0222195 A1 | 8/2017 | Hartl | |
| 2018/0333155 A1 * | 11/2018 | Hall | A61B 17/072 |
| 2019/0209725 A1 * | 7/2019 | Henniges | A61L 2/24 |
| 2019/0328598 A1 * | 10/2019 | Mangiardi | B08B 7/0057 |
| 2021/0067616 A1 * | 3/2021 | Penfold | A45C 11/00 |
| 2021/0215990 A1 * | 7/2021 | Parker | B32B 17/10055 |
| 2022/0168039 A1 * | 6/2022 | Worrell | A61B 18/085 |
| 2022/0226013 A1 * | 7/2022 | Hall | A61B 90/90 |
| 2022/0241027 A1 * | 8/2022 | Shelton, IV | A61B 18/1206 |

FOREIGN PATENT DOCUMENTS

| | | |
|---|---|---|
| DE | 102007048402 | 4/2009 |
| DE | 102009022687 | 7/2010 |
| EP | 2180773 | 4/2010 |
| JP | 2016042331 | 3/2016 |
| WO | 2012088141 | 6/2012 |
| WO | 2017062466 | 4/2017 |

OTHER PUBLICATIONS

English translation of International Preliminary Report on Patentability from corresponding International Application PCT/EP2018/081439 dated Jun. 4, 2020, 10 pages.

Search Report from corresponding International Application PCT/EP2018/081439 dated Feb. 21, 2019.

\* cited by examiner

AUTOCLAVABLE MEDICAL DEVICE AND ACTUATION MEANS FOR AN AUTOCLAVABLE MEDICAL DEVICE

CROSS REFERENCE TO RELATED APPLICATIONS

This application is a continuation of International Application PCT/EP2018/081439 filed Nov. 15, 2018, which claims benefit of German Application 10 2017 127 723.4 filed Nov. 23, 2017, the entire contents of all of which are incorporated by reference herein

BACKGROUND

1. Field of the Invention

The invention relates to a disinfectable or sterilizable, in particular autoclavable device, in particular a medical device, which comprises electronic components. The device in particular comprises an electric motor and/or a turbine, in particular a compressed air turbine and/or an electrical lighting device. The invention further relates to wearable devices such as smart watches or fitness trackers, and to portable electronic monitoring devices for implants. The invention also relates to an actuation means for an autoclavable device.

2. Description of Related Art

Medical devices are, in practice, often sterilized by autoclaving. For this purpose, the medical device or parts thereof are introduced into an autoclave, in order to be sterilized there using steam at high temperature (typically 134° C.) and elevated pressure (typically 2 bar).

Autoclaving is highly efficient against germs and enables safe sterilization even of hidden areas of the medical device, i.e. areas that are not accessible manually.

What is important during autoclaving is that the steam can reach all surfaces of the medical device.

The provision of electrically operated medical devices that are autoclavable as a whole, especially those that include electronics, is complex and costly.

The only option in practice is to design only part of the medical device so as to be autoclavable, in particular a part that does not include any electrical or electronic components. For this purpose, the medical device has to be disassembled and can be sterilized by autoclaving only in part, of course.

So it would be desirable to make the electrical and electronic components of a medical device so as to be autoclavable, too. This applies in particular to the actuation means, especially the switch for switching the medical device on and off.

In this regard, it may be considered to seal the housing of the medical device, so that electrical and/or electronic assemblies are located within a hermetically sealed autoclavable housing.

It is problematic, however, to design the housing such that it withstands a large number of autoclaving processes and at the same time to have accessible actuation means.

Even small amounts of water vapor can cause malfunctions or failure of the electronics of the medical device. To rule out condensation of water vapor, the water content within the housing has to be below the threshold value for the dew point over the entire service life of the device. Typically, this limit is a water content of max. 5000 ppm of the enclosed gas atmosphere.

From watch industry, seals are known, in particular polymer seals such as O-rings, which enable a watch housing to withstand high pressures under water, while such a watch can nevertheless be provided with buttons or rotary crowns accessible to the user. However, the employed polymer seals are usually gas-permeable at least to a certain extent, so that steam will penetrate therethrough in every autoclave cycle.

Now, if the water concentration within the housing rises until reaching the dew point, this may result in malfunctions or damage.

Thus, polymeric seals usually allow to achieve not more than a few hundred autoclaving cycles before the medical device has to be revised or replaced.

Furthermore, capacitive sensor areas made of glass are known, in particular from displays such as those of smartphones. Touching the display locally changes the capacity of an electronic component, whereby the position of the finger on the display can be determined. Operating components on glass ceramic cooktops are also designed according to a similar principle, namely the principle of a capacitive switch.

However, housing materials used in medical technology, in particular austenitic stainless steel, are difficult to combine with glass or glass ceramic sheets, because of the very different coefficient of linear thermal expansion thereof.

Glass sheets for a housing, behind which a commercially available capacitive proximity switch can be arranged, for example, which are known from practice, usually also lack sufficient gas-tightness to withstand a large number of autoclaving cycles. Such glass sheets are in particular bonded to the housing using polymeric adhesives.

In the case of non-medical devices such as fitness trackers and smart watches it is also problematic to design switches, in particular capacitive proximity switches, in a way so that sufficient tightness is ensured and at the same time a sterilizable housing is provided which in particular has no grooves around the switch, where dirt and thus germs might accumulate.

SUMMARY

Given the above, the invention is based on the object of providing a device which is easy to disinfect and/or sterilize and which at the same time has a sealed housing in which electrical and/or electronic components are accommodated.

The invention is in particular based on the object of providing an autoclavable device comprising an actuation means, which is designed for a high number of autoclaving cycles, in particular for more than 500 autoclaving cycles.

The object of the invention is already achieved by a disinfectable and/or sterilizable, in particular autoclavable device and by an actuation means for a device.

The invention relates to a disinfectable and/or sterilizable, in particular autoclavable device.

More particularly, the invention relates to a medical device.

In particular, the invention relates to an autoclavable device that includes an electric motor, a turbine, and/or a device for emitting electromagnetic radiation, in particular a light source. For example, the invention relates to a medical drill, in particular a dental drill, a saw or a file. Furthermore, the invention may also relate to a lighting device, in particular a medical lighting device, for example a diagnostic and/or surgical light, a dental curing device, and/or to a device for exciting and/or evaluating fluorescence. The invention may also relate to an electrosurgical device, in particular a medical device for electrical coagulation, or a laser scalpel.

Furthermore, the device may be in the form of a wearable device, for example equipped with a bracelet.

The device can also be in the form of a fitness tracker or smart watch. Such wearable devices usually comprise a display. In addition to being actuated via a touch-sensitive screen, such devices often moreover include other actuation means, in particular capacitive switches or contacts for measuring bodily functions such as heart rate.

Within the meaning of the invention, autoclavable device refers to that part of a device which is autoclavable as a whole. This may in particular be the handpiece of a device, which includes an actuation means.

The housing of the device is made of metal, at least portions thereof, and is hermetically sealed at least in part, so that electrical and/or electronic components can be accommodated inside the housing.

According to the invention, the housing comprises an electrical conductor which is embedded in an inorganic fixing material. The electrical conductor is in particular fused into the fixing material. The fixing material is in particular an electrically insulating fixing material such as a glass, a glass ceramic, and/or a ceramic. Combinations thereof are also possible, as are multi-layer structures of different fixing materials.

The electrical conductor defines an electrical feedthrough with the fixing material, extending from an inner side of the housing and through at least a portion of the fixing material.

The combination of a metal housing with a fused-in electrical feedthrough permits to provide a device which is sealed and at the same time easy to disinfect or sterilize, and which may in particular also come in the form of a smart watch or fitness tracker.

The electrical conductor is preferably bonded to the housing itself, i.e. a wall of the housing, by being fused into the fixing material. The electrical conductor may in particular be fused into an upper or lower housing half (e.g. of a smart watch or a fitness tracker, or of the handpiece of a medical device) using the fixing material.

An electrical feedthrough in the sense of the invention is understood to mean an electrical conductor, preferably made of metal, in particular a pin, which extends through an opening in the metal housing, at least portions thereof, in particular enclosed in a glass seal.

Thus, the electrical conductor in combination with the fixing material forms the electrical feedthrough, the fixing material serving as an insulator against the adjacent metallic housing and at the same time as a hermetic seal.

Preferably, a glass and/or a glass ceramic is used as the fixing material. In particular a glass or a glass ceramic that can be fused between 800 and 1200° C. can be used.

According to the invention, the electrical feedthrough is part of a sensor, in particular of an actuation means.

An actuation means in the sense of the invention is understood to mean a component that can be operated manually by the user, possibly also with the aid of a manipulating means such as a stylus, which can be used to set and/or control the operation of the device. For this purpose, a sensor is provided which allows to detect an actuation by the user.

The actuation means has the function of initiating and/or setting operating states of the device. The actuation means in particular defines an interface of the device for the user. Operating states include, for example, switching on and/or switching off of the device or of functions thereof. Operating states beyond that are of course also possible, for example the setting of illuminance, and/or the setting of a motor speed, and/or the setting of a turbine speed, etc.

In addition to the functionality of the electrical feedthrough as an actuation means, the electrical feedthrough may also be used to measure bodily functions. For example, the electrical feedthrough may comprise a sensor surface or may be connected to a sensor surface that serves as a skin electrode for measuring the user's heart rate, for example.

In the simplest case, the sensor is in the form of a switch for switching on and off the device.

The electrical feedthrough forms at least a component of the sensor of the actuation means, as will be explained below by way of examples.

The feedthrough may in particular be part of a circuit which can be closed, thus defining a switch.

Also, the feedthrough in the form of a capacitor may be part of an electronic circuit for switching on and/or controlling functions of the autoclavable device. For example, a metal pin disposed in an inorganic fixing material already constitutes a cylindrical capacitor, due to the different dielectric constants of the inorganic material and the metal pin.

According to a first embodiment of the invention, the electrical conductor extends only through a portion of the inorganic fixing material and is spaced apart from an outer surface of the fixing material.

In this embodiment, the electrical conductor thus terminates within the fixing material, seen from the interior of the housing. So, the fixing material covers the conductor on the outer surface of the housing, which in particular further improves the tightness and may under certain circumstances reduce the risk of short circuits. In addition, the risk of germ accumulation can be reduced by eliminating a material transition from the conductor to the fixing material. Furthermore, this technical solution allows design freedom for the designers of the device and/or improves user guidance.

In another embodiment of the invention, the electrical feedthrough extends to an upper surface of the inorganic fixing material, in particular to an outer surface of the housing. This may also be desirable in terms of user guidance.

A feedthrough configured in this way may thus form part of an actuation means which effects a switching operation by closing a circuit. For example, the electrical feedthrough may define a switch with the housing and/or with another electrical feedthrough.

A switching operation may, for example, be effected by a contact member forming part of the switch and made of electrically conductive material, which closes the switch when being actuated.

The contact member may in particular be in the form of a rocker or a dome arranged above the feedthrough.

So the sensor is in the form of a switch. Electrical current for operating the device can flow directly through the sensor in the form of a switch. An evaluation circuit can be dispensed with in this embodiment of the invention.

It is also possible to illuminate the fixing material from behind, i.e. from the interior of the housing. The lighting state may in particular depend on the operating state. When the device is in its off state, the lighting may, so to speak, indicate the switch and/or sensor. Also, a changed lighting state, for example changed luminosity and/or color, may indicate the device's response to an actuation by the user. This illumination is made possible due to the fact that the feedthrough hermetically seals the housing. The light sources required for this purpose, e.g. LEDs and/or OLEDs, and the associated control electronics can be integrated into the interior of the housing and can thus be autoclaved together with the entire device.

According to one embodiment of the invention, a gas-tightly sealed dome is provided, which is in particular made of metal and is gas-tightly joined to the housing or to a component connected to the housing.

This prevents water vapor from ingressing during autoclaving.

In another embodiment, the dome is provided with at least one opening for the entry of water vapor so that the interior of the dome can also be reached by water vapor during autoclaving.

Instead of an electrically conductive contact member which is actuated by the user to close the circuit, it is contemplated according to another embodiment of the invention that a circuit is closed solely by the hand or fingers of the user. In this exemplary embodiment, electrical current can flow through the user's finger or hand to initiate a switching operation. A separate contact member is not provided in this embodiment of the invention. This embodiment has the advantage that an external contact member for closing the circuit can be dispensed with. However, the electrical current for operating the device cannot flow through the sensor.

In another embodiment of the invention, the electrical feedthrough is part of an electronic circuit which is in the form of an actuation means based on a change in an inductance or capacitance.

The sensor is in particular implemented as a proximity switch, which triggers a signal change, in particular a switching signal, when the user approaches his or her hand or finger, for example.

The sensor is preferably in the form of a capacitive proximity switch. In this case, the capacitor defined by the feedthrough is preferably part of the capacitive proximity switch.

The capacitive proximity switch of this type is in particular implemented as an oscillator circuit, the frequency of which changes upon approach, which in turn is detected by an electronic circuit and converted into a switching signal.

The capacitance of the capacitor defined by the electrical feedthrough changes due to the different dielectric constant of the user's finger or hand or of another manipulating means. This in turn results in the change in frequency which is detected by the electronic circuit. Such electronic circuits, in particular circuits whose sensitivity adjusts automatically to changing ambient conditions, are known to the person skilled in the art.

The capacitor defined by the feedthrough preferably provides the capacitance of the oscillator circuit, so that a further capacitor can be dispensed with in the oscillator circuit, as is contemplated according to a preferred embodiment of the invention.

In a refinement of the invention, the fixing material together with the electrical conductor, i.e. the electrical feedthrough, is disposed within a metal ring which in turn is placed in an opening of the housing of the autoclavable device. The electrical conductor is joined to the metal ring by being fused into the fixing material.

In this way, the actuation means can be provided as a modular component which then only has to be integrated into the housing. It is therefore not necessary to perform the glass sealing process of the feedthrough at the site where the housing is assembled.

The metal ring may in particular be welded or soldered to the metal housing. Preferably, a metal ring is used which has a coefficient of linear thermal expansion α (always @20° C. unless otherwise stated) which differs from the material of the adjacent housing by less than 3, preferably less than 1 ppm/K.

The metal ring is in particular made of titanium or of stainless steel, especially austenitic stainless steel. Preferably, the metal ring is made of the same material as the housing.

It goes without saying that in the sense of the invention the metal ring does not necessarily have to be circular, but may have any arbitrary shape, in particular an angular shape.

In one embodiment of the invention, the metal ring has a coefficient of linear thermal expansion greater than that of the fixing material, so that the feedthrough is in the form of a compression glass feedthrough. Due to the greater thermal expansion of the metal ring compared to that of the glass, the latter is put under compression during cooling. In particular, the metal ring may be made of a material having a coefficient of linear thermal expansion that is greater than the coefficient of linear thermal expansion of the fixing material by at least 5, preferably at least 8 ppm/K.

According to another embodiment of the invention it is contemplated that the expansion coefficients of the metal ring, of the inorganic fixing material, and/or of the electrical conductor are matched to one another.

For example, a metal ring can be used which has a coefficient of linear thermal expansion α that differs from that of the fixing material by less than 5, preferably less than 3 ppm/K.

In this embodiment of the invention, a material with linear thermal expansion of α<12 ppm/K is preferably used for the metal ring. In particular titanium or a titanium alloy can be used.

In one refinement of the invention, the device includes an actuation means comprising a plurality of electrical feedthroughs. This in particular allows to initiate different functions or to control a function, such as speed.

The actuation means may in particular be designed such that it defines a position on a surface of the actuation means. This may be achieved, for example, by at least one feedthrough which extends parallel to a surface of the device at least in sections thereof.

Furthermore, the position of a manipulating means such as a finger can be determined by using a plurality of electrical feedthroughs.

The actuation means may be configured such that a plurality of different operating states of the device can be set on the basis of a direction and/or distance of an actuating movement.

In the case of a plurality of feedthroughs, a functionality can be controlled, for example, on the basis of whether these feedthroughs are successively swiped by a movement from the right or from the left. Furthermore, an operating state such as the speed of a drill may also be controlled through the distance of a manipulating means such as a finger.

The inventors have found that a feedthrough comprising an inorganic fixing material allows in a very simple manner to provide an actuation means on an outer surface of the device, which enables the device along with the actuation means to be sterilized in an autoclave and to withstand a large number of autoclaving cycles.

The invention further relates to an actuation means for the device described above. The actuation means is in particular implemented as a switch.

The actuation means thus comprises an electrical feedthrough consisting of an electrical conductor embedded in a fixing material.

The actuation means preferably comprises a metal ring which can be disposed in the opening of the housing of a device, in particular of an autoclavable medical device.

BRIEF DESCRIPTION OF THE DRAWINGS

The subject-matter of the invention will be explained in more detail below by way of schematically illustrated exemplary embodiments and with reference to the drawings of FIGS. 1 to 14.

DETAILED DESCRIPTION

Figure 1:
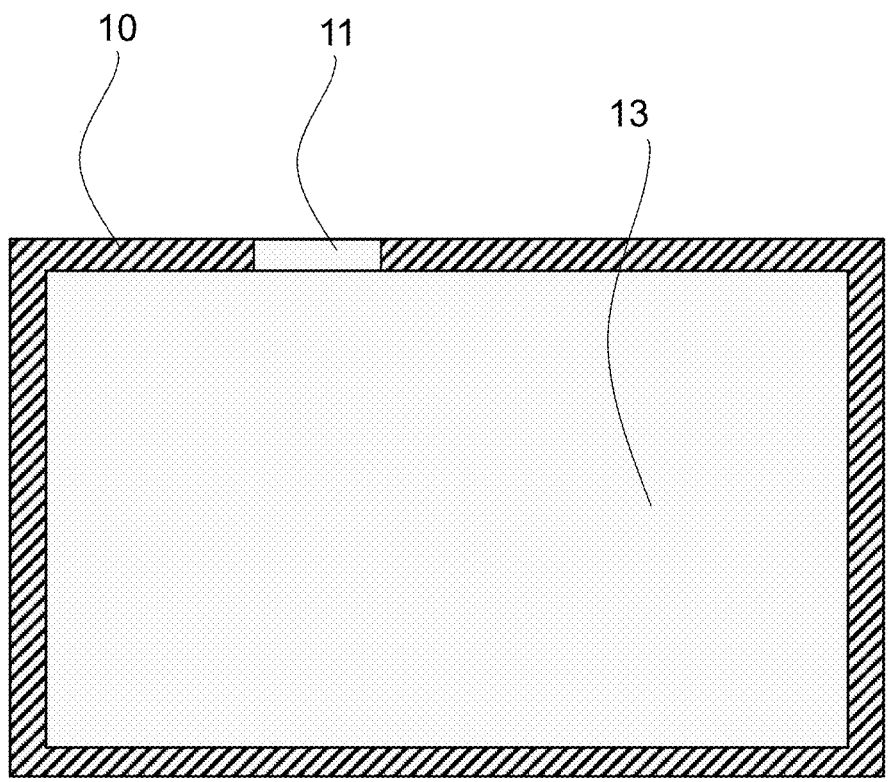
FIG. 1 schematically illustrates the housing of a medical device which is to be equipped with an actuation means according to the invention.

FIG. 1 schematically illustrates the housing 10 of an autoclavable medical device.

Housing 10 is made of metal, in particular stainless steel such as an austenitic stainless steel, in particular the alloy 1.4404. The housing has an interior 13 where in particular electrical and/or electronic components (not shown) may be accommodated.

Furthermore, the housing 10 has an opening 11 which is used to accommodate an actuation means for the autoclavable medical device. The opening 11 may in particular be in the form of a bore.

The wall thickness of the housing is preferably from 0.3 to 5 mm, particularly preferably from 0.8 to 2 mm, at least in the vicinity of the opening.

Figure 2:
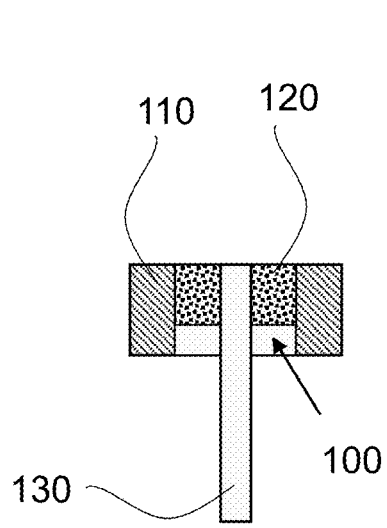
FIGS. 2 and 3 show two different exemplary embodiments of an actuation means that can be used.

FIG. 2 shows a first exemplary embodiment of a feedthrough 100 which may be used as an actuation means.

Feedthrough 100 consists of a fixing material 120 made of glass, in which a metal pin 130 is embedded, which defines an electrical conductor.

Pin 130 preferably has a diameter from 0.2 to 3 mm. The fixing material 120 has a thickness of preferably 0.5 to 5 mm and/or a diameter between 0.7 and 5 mm.

As provided in one embodiment of the invention, a lighting device (not shown) may be accommodated inside the housing, such that light passes through the fixing material 120 to the outside. For example an illuminated actuation means and/or a visual indication of an operating state of the medical device may be implemented in this way.

Fixing material 120 and pin 130 form a cylindrical capacitor in the area of the feedthrough 100.

The feedthrough 100 is surrounded by a metal ring 110 which is intended to be inserted into the opening (11 in FIG. 1) of the housing.

This metal ring 110 can be joined to the housing in a gas-tight manner, for example by soldering or welding, so that a hermetically sealed housing is obtained. The metal ring 110 is therefore preferably made of the same material as the adjacent housing.

In the embodiment of FIG. 2, the pin 130 extends as far as to the upper surface of the fixing material 120.

Figure 3:
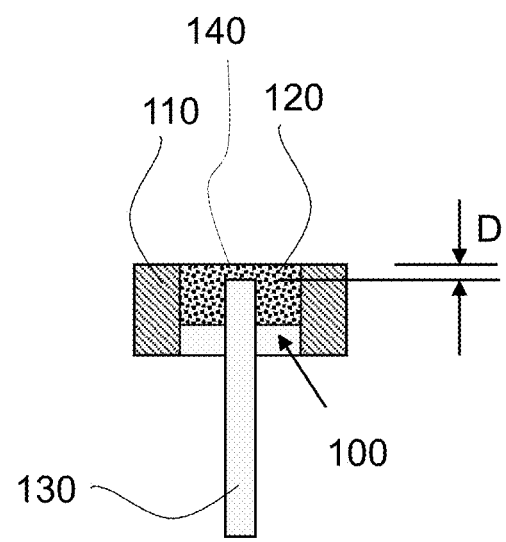

In the embodiment of FIG. 3, by contrast, the end face of pin 130 is spaced apart from the upper surface 140 of the fixing material 120 by a distance D.

Therefore, the pin 130 cannot be electrically connected from outside in this embodiment of the invention. Thus, the actuation means according to the embodiment of FIG. 3 cannot be a switch that triggers a switching operation by closing a circuit.

Rather, the sensor comprising the electrical feedthrough according to FIG. 3 is in the form of a capacitive proximity sensor.

Referring to FIGS. 4 to 7, an embodiment of an actuation means in the form of a capacitive proximity switch will be explained in different operating states thereof.

Figure 4:
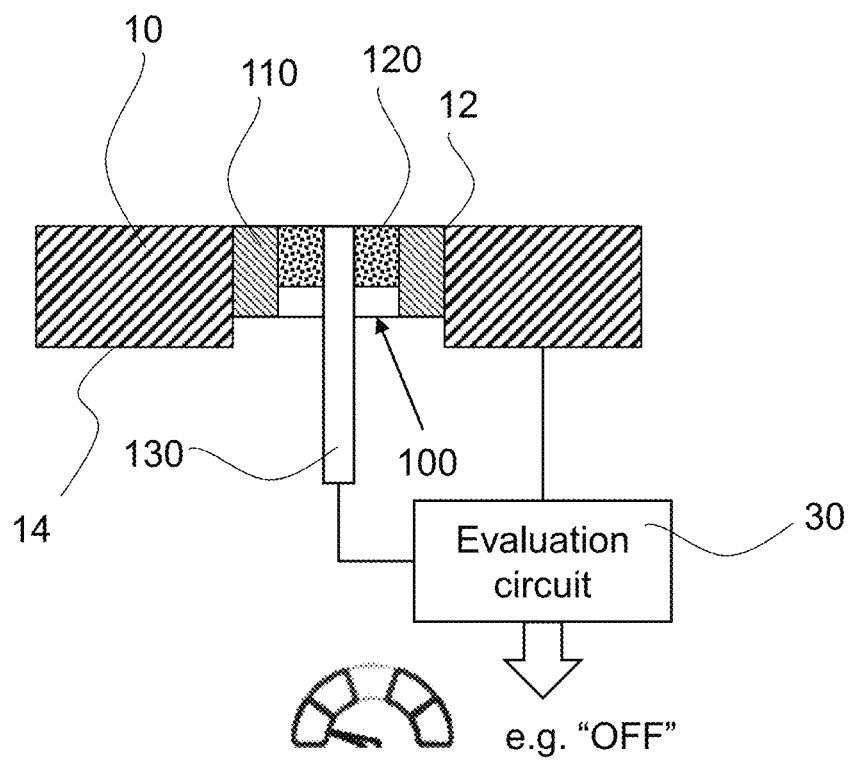
FIGS. 4 to 7 are intended to explain in more detail the functioning of an individual electrical feedthrough which is used as an actuation means and forms a capacitive proximity sensor and, in different operating states.

As can be seen in FIG. 4, the metal ring 110 has now been installed in the housing 10.

The metal ring 110 is preferably welded or soldered to the wall of housing 10 in the contact area 12 in order to form a gas-tight joint. The use of metal ring 110 provides for simple installation, since the material of the metal ring 110 can be matched to the material of the housing 10.

The embodiment of FIGS. 4 to 7 corresponds to the embodiment of FIG. 2 in which the pin 130 extends as far as to the upper surface of the fixing material 120.

The pin 130 extends from the inner side 14 of the housing 10 through the fixing material. As described above, the electrical feedthrough 100 designed in this way defines a capacitor.

Pin 130 is connected to an evaluation circuit 30 which comprises an oscillator circuit in which the feedthrough 100 serves as a capacitor of an electrical resonant circuit.

FIG. 4 shows the actuation means in a non-actuated state. This may correspond to a switching state "OFF".

Figure 5:
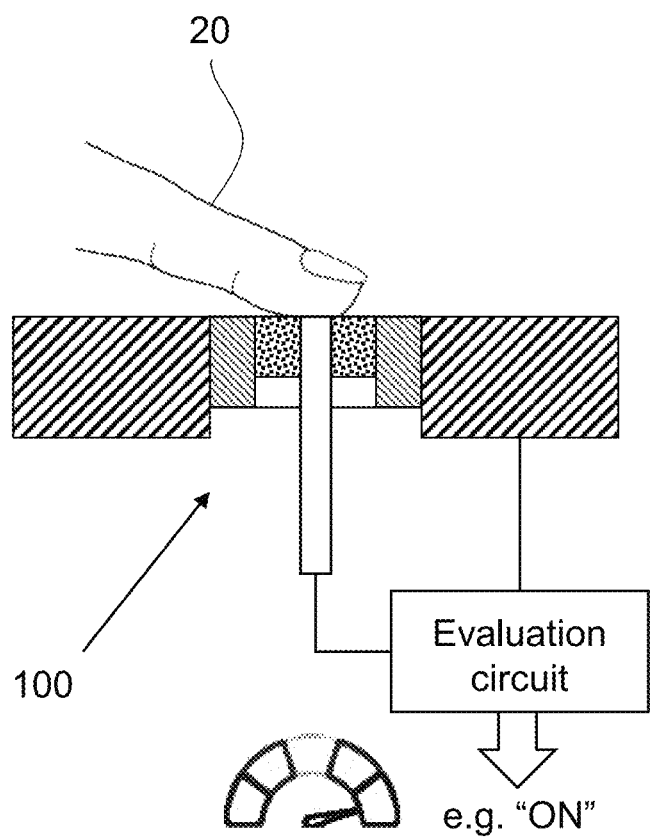

As shown in FIG. 5, an actuating member, in particular a finger 20, can be placed on the feedthrough 100.

Due to the different dielectric constant of the finger 20 compared to air, the frequency of the oscillator circuit will change which in turn can be detected by the evaluation circuit 30, so that the switching signal is now "ON", for example.

Figure 6:
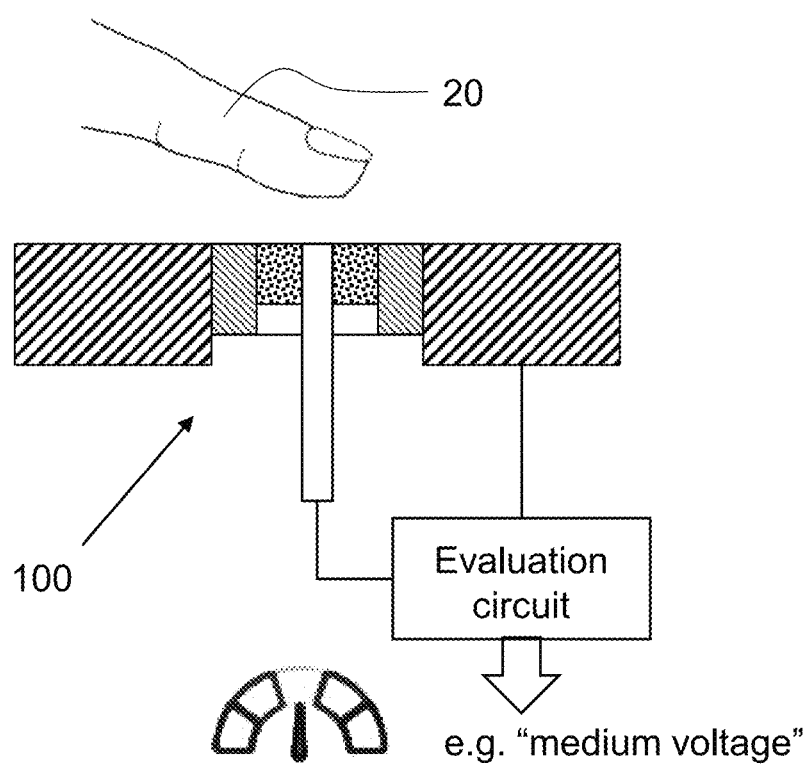
Figure 7:
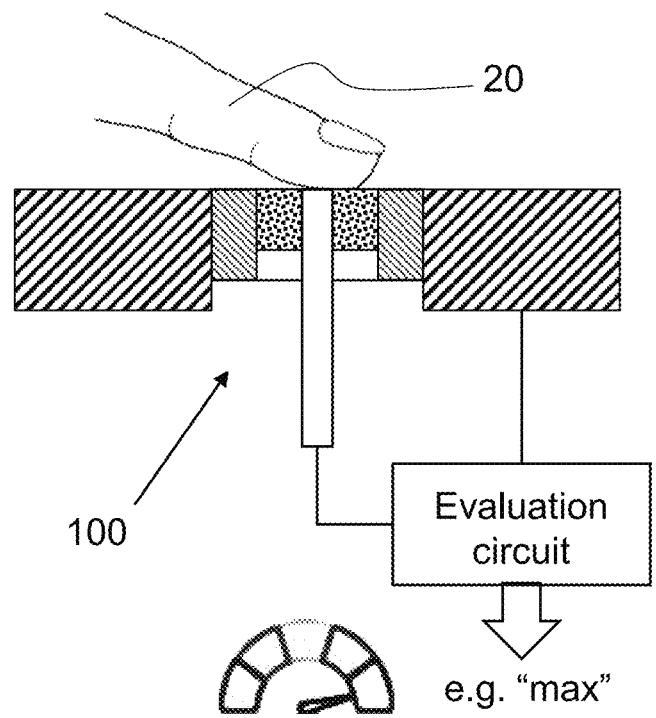

As illustrated in FIGS. 6 and 7, a further embodiment of the invention contemplates to provide the actuation means in the form of a proximity sensor, via which a plurality of operating states can be set, i.e. not only "ON" and "OFF".

As shown in FIG. 6, a signal is already generated when the finger 20 approaches the feedthrough 100, which may correspond to a medium operating state such as a medium voltage, power output, speed, etc., for example.

As furthermore shown in FIG. 7, a maximum power output may then be set when the finger 20 touches the feedthrough 100.

It goes without saying that this adjustment can be effected in a continuously variable manner or in steps.

Figure 8:
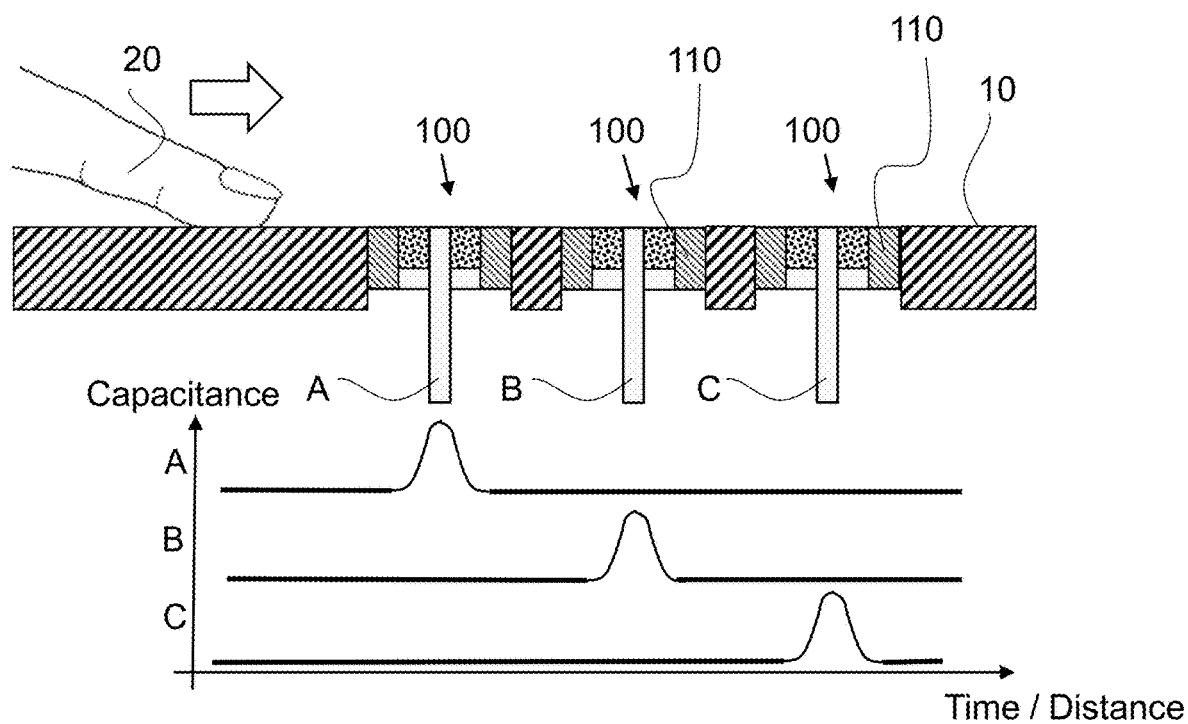
FIG. 8 shows an embodiment comprising a plurality of feedthroughs arranged next to one another, and the signal waveform resulting when swiping over these feedthroughs.

FIG. 8 shows how a plurality of feedthroughs 100 are arranged next to one another in a housing 10.

In this exemplary embodiment, each of the feedthroughs 100 is arranged in a separate opening in the housing 10 using a respective metal ring 110.

As shown below the feedthroughs 100, direction-related information can be detected when swiping the finger 20 over the feedthroughs in areas A to C, in this exemplary embodiment from left to right, on the basis of temporally offset changes in capacity. This allows to implement switching steps or almost continuous controlling.

Figure 9:
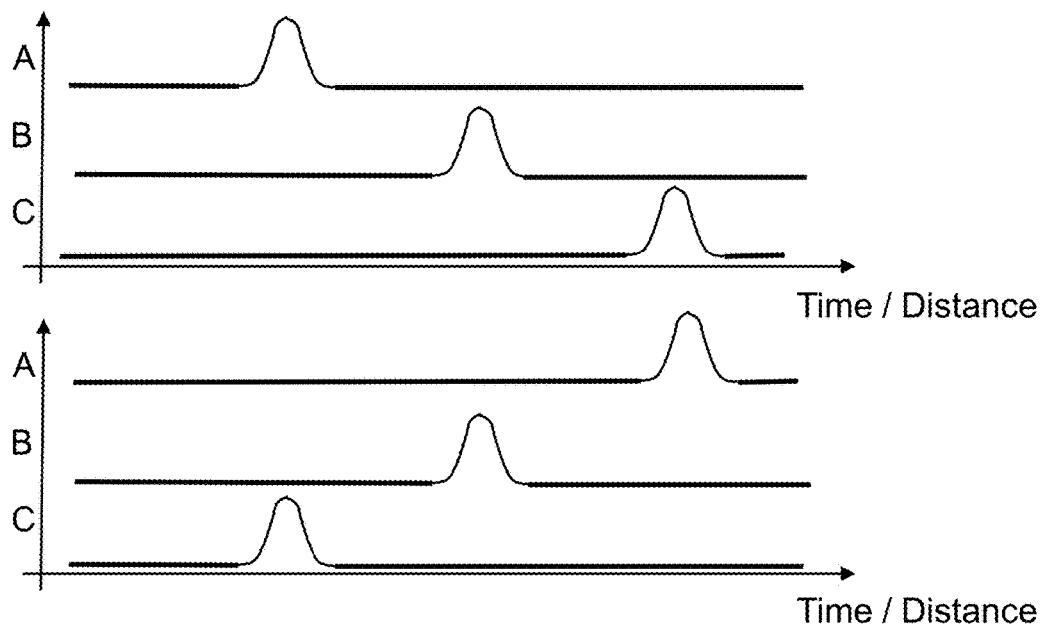
FIG. 9 shows the signal waveform when swiping from different directions.

FIG. 9 shows the change in capacity when swiping over the feedthroughs either from the right or from the left. Depending on the direction, the signal waveform is different, so that, for example, an output power may be increased or decreased depending on the direction in which the finger swipes over the areas A to C of an actuation means.

Figure 10:
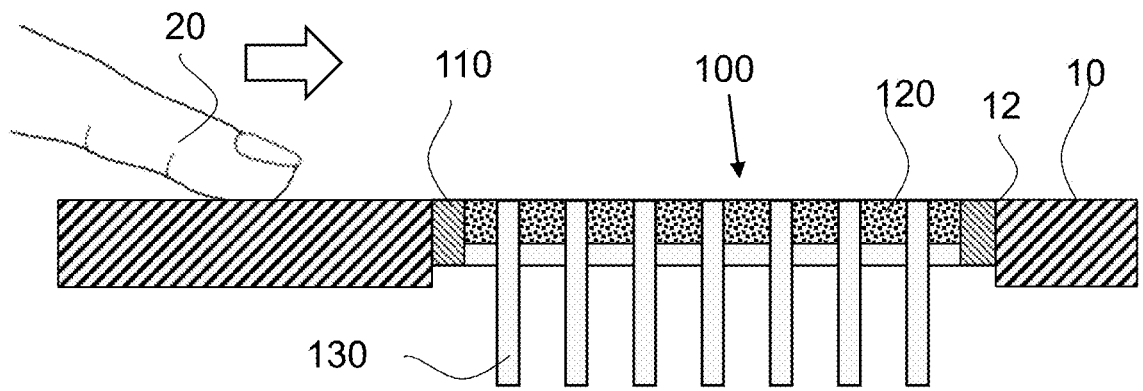
FIG. 10 shows an alternative embodiment of an actuation means comprising a plurality of electrical conductors in a single feedthrough.

FIG. 10 shows an alternative embodiment of the invention, in which a plurality of pins 130 are arranged in a single feedthrough 100 using the fixing material 120.

The fixing material is again disposed in a ring 110, as in the previously illustrated exemplary embodiment.

In this embodiment of the invention, it is in particular possible to arrange a large number of electrical conductors in a single feedthrough, in particular more than five, for detecting in particular the position and/or direction of the finger 20 when swiping over it.

Figure 11:
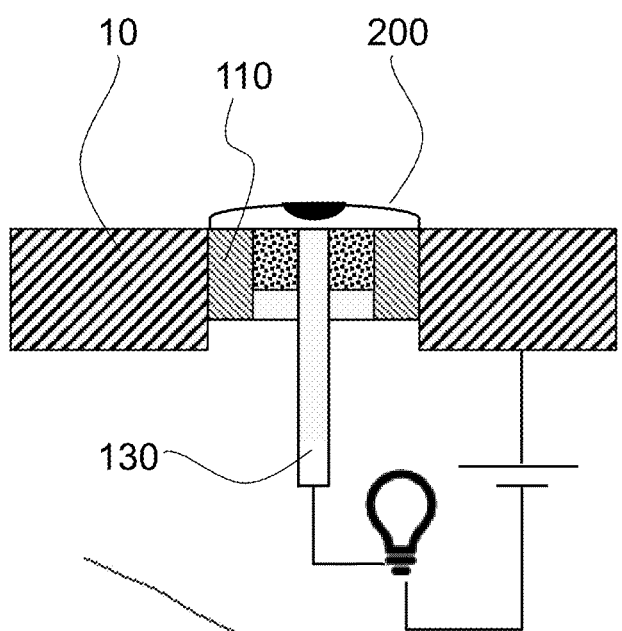
FIGS. 11 and 12 are intended to explain in more detail an alternative embodiment of an actuation means in which a circuit is closed by pressing a contact member.
Figure 12:
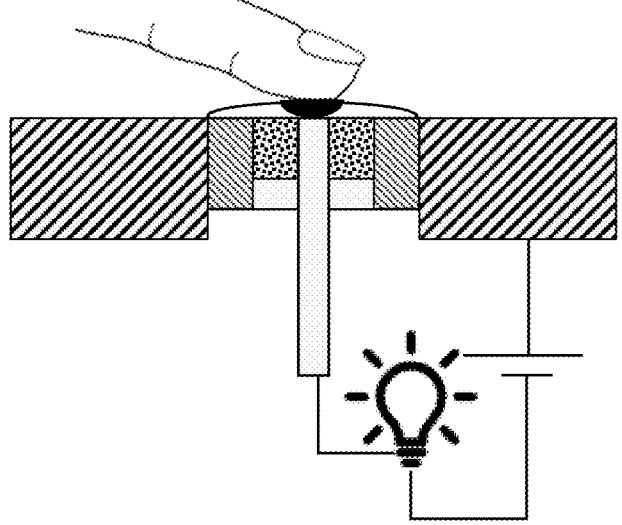

FIGS. 11 and 12 schematically illustrate an alternative exemplary embodiment of the invention.

In this embodiment, the actuation means is in the form of a switch, which generates a switching signal by closing a circuit.

In this exemplary embodiment, a contact member is applied to the metal ring 110, which is implemented as a switching membrane in the form of a dome 200 in this exemplary embodiment.

By pressing the dome 200, an electrical circuit is closed and a switching signal is generated, as shown in FIG. 12.

In this embodiment of the invention, the dome 200 is in the form of a metallic membrane that is connected to the metal ring 110 by welding or soldering. This prevents the ingress of water vapor during autoclaving.

The invention permits to provide, in a simple manner, an autoclavable device, in particular an autoclavable medical device which comprises a hermetically sealed housing with electrical or electronic components and withstands a large number of autoclave cycles.

The invention can also be used for smart watches and fitness trackers.

Figures 13, 14:
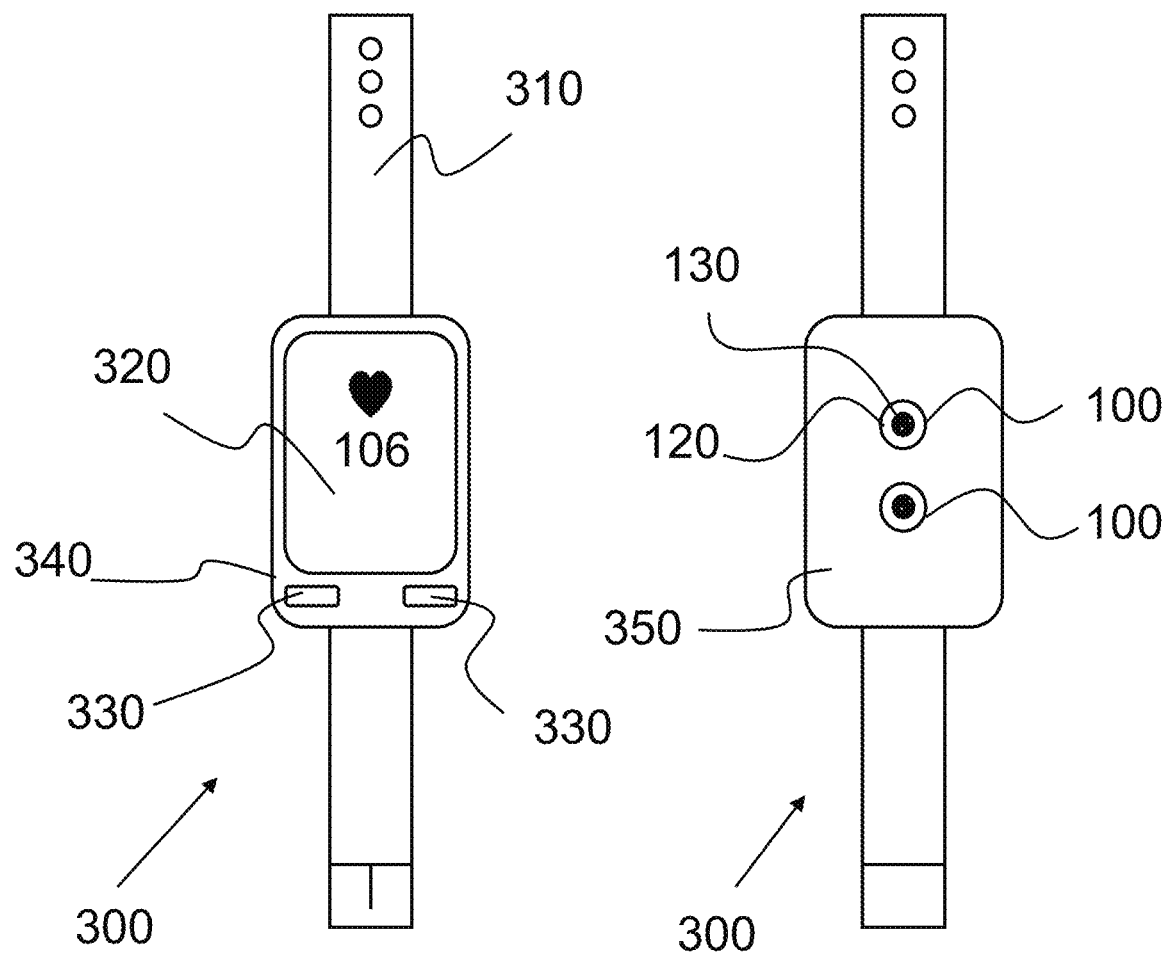
FIG. 13 is a schematic view of the front face.
FIG. 14 is a schematic view of the rear face of an exemplary embodiment of a smart watch according to the invention.

FIG. 13 is a schematic view of a smart watch 300 which is also a fitness tracker.

Smart watch 300 is wearable on the wrist by the user, using the bracelet 310.

Via display 320, the user can derive bodily functions such as heart rate.

In addition to the display 320, the upper housing half 340 includes actuation means 330 which allow to control the functions of the smart watch. Separate actuation means 330 have the advantage that they are easier to control than a touch display, for example when jogging.

The upper housing half 340 is made of metal, in particular stainless steel.

The actuation means 330 are preferably in the form of a capacitive proximity switch according to the embodiment of FIG. 3. So the electrical feedthrough terminates at a distance from the surface of the actuation means, so that the actuation means 330 appear in the form of glass surfaces preferably flush with the upper housing half 340.

The electrical feedthrough is located below the glass surface of the actuation means 330 and is preferably not visible.

FIG. 14 is a view of the rear face of the smart watch 300.

The lower housing half 350 is also made of metal. Feedthroughs 100 each one comprising a pin 130 fused into a fixing material 120 are disposed in the lower half of the housing.

Pins 130 contact the skin of the user and serve as skin electrodes, e.g. for heart rate measurement. Pins 130 preferably protrude from the housing to ensure good contact with the skin.

The combination of metal and glass provides for good sealing of the smart watch and at the same time allows for easy sterilization and cleaning due to the smooth inorganic surfaces.

LIST OF REFERENCE NUMERALS

10 Housing
11 Opening
12 Contact area
13 Interior
14 Inner side
20 Finger
30 Evaluation circuit
100 Feedthrough
110 Metal ring
120 Fixing material
130 Pin
140 Upper surface
200 Contact member
300 Smart watch
310 Bracelet
320 Display
330 Actuation means
340 Upper housing half
350 Lower housing half

What is claimed is:

1. An autoclavable device, comprising:
a metal housing having an interior and exterior;
an electrical feedthrough extending from the interior towards the exterior of the metal housing, wherein the electrical feedthrough is a component of a sensor or activation device;
an inorganic fixing material; and
an electrical conductor fused into the inorganic fixing material,
wherein the electrical conductor is embedded in and affixed in the metal housing by the inorganic fixing material to define the electrical feedthrough.

2. The autoclavable device of claim 1, wherein the inorganic fixing material is glass and/or glass ceramic.

3. The autoclavable device of claim 1, wherein the electrical conductor extends through a portion of the inorganic fixing material and is spaced apart from an outer surface of the inorganic fixing material.

4. The autoclavable device of claim 1, wherein the electrical conductor extends to an outer surface of the inorganic fixing material.

5. The autoclavable device of claim 1, wherein the electrical feedthrough extends to an outer surface of the metal housing.

6. The autoclavable device of claim 1, wherein the sensor or activation device is a proximity switch or a capacitive proximity switch.

7. The autoclavable device of claim 1, wherein the sensor or activation device is a capacitive sensor, and the electrical feedthrough is a capacitor of an electronic circuit of the capacitive sensor.

8. The autoclavable device of claim 1, wherein the sensor or activation device is a switch.

9. The autoclavable device of claim 8, wherein the switch comprises a contact member made of electrically conductive material, the contacting member being configured to close the switch when actuated.

10. The autoclavable device of claim 9, wherein the contact member is a dome arranged above the electric feedthrough.

11. The autoclavable device of claim 10, wherein the dome is a gas-tightly sealed dome or dome having an opening for entry of water vapor.

12. The autoclavable device of claim 1, further comprising: a light source arranged in the interior of the metal housing to emit light through the inorganic fixing material to the exterior of the metal housing.

13. The autoclavable device of claim 12, wherein the light source is an indicator sensor or activation device.

14. The autoclavable device of claim 1, further comprising a metal ring accommodated in an opening of the metal housing, wherein the inorganic fixing material is glass, and wherein the electrical feedthrough is disposed in the metal ring to define a compression glass feedthrough with the metal ring.

15. The autoclavable device of claim 14, wherein the metal ring has a coefficient of thermal expansion that differs from a coefficient of thermal expansion of the metal housing by less than 3 ppm/K at 20° C.

16. The autoclavable device of claim 1, wherein the electrical conductor is a pin.

17. The autoclavable device of claim 1, further comprising a plurality of electrical feedthroughs.

18. The autoclavable device of claim 1, wherein the device configured and adapted for a use selected from a group consisting of a medical drill, a dental drill, a medical saw, a medical file, a medical lighting device, a diagnostic light, a surgical light, a dental curing device, a device for excitation and/or evaluation of fluorescence, an electrosurgical device, an electrical coagulation device, a laser scalpel, a smart watch, and a fitness tracker.

* * * * *

UNITED STATES PATENT AND TRADEMARK OFFICE
CERTIFICATE OF CORRECTION

PATENT NO. : 11,684,704 B2
APPLICATION NO. : 16/882830
DATED : June 27, 2023
INVENTOR(S) : Robert Hettler It is certified that error appears in the above-identified patent and that said Letters Patent is hereby corrected as shown below:

On the Title Page

In item (63) Related U.S. Application data, delete "May 31, 2019" and insert -- November 15, 2018 --

Signed and Sealed this
Twenty-second Day of August, 2023

*Katherine Kelly Vidal*

Katherine Kelly Vidal
*Director of the United States Patent and Trademark Office*